United States Patent
Fujimura et al.

(10) Patent No.: US 7,206,435 B2
(45) Date of Patent: Apr. 17, 2007

(54) REAL-TIME EYE DETECTION AND TRACKING UNDER VARIOUS LIGHT CONDITIONS

(75) Inventors: Kikuo Fujimura, Palo Alto, CA (US); Zhiwei Zhu, Troy, NY (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 633 days.

(21) Appl. No.: 10/396,285

(22) Filed: Mar. 24, 2003

(65) Prior Publication Data

US 2004/0005083 A1 Jan. 8, 2004

Related U.S. Application Data

(60) Provisional application No. 60/367,878, filed on Mar. 26, 2002.

(51) Int. Cl.
*G06K 9/00* (2006.01)
(52) U.S. Cl. .................................. 382/117
(58) Field of Classification Search ............ 382/117
See application file for complete search history.

(56) References Cited

U.S. PATENT DOCUMENTS

| | | | |
|---|---|---|---|
| 6,421,463 B1 * | 7/2002 | Poggio et al. | 382/224 |
| 6,539,100 B1 * | 3/2003 | Amir et al. | 382/117 |
| 6,714,665 B1 * | 3/2004 | Hanna et al. | 382/117 |

FOREIGN PATENT DOCUMENTS

| | | |
|---|---|---|
| JP | 09-243327 | 9/1997 |
| JP | 10-221016 | 8/1998 |
| JP | 2002-008020 | 1/2002 |

OTHER PUBLICATIONS

Website URL: http://imagers.gsfc.nasa.gov/ems/infrared.html.*
S. Baluja, D. Pomerleau. Non-Intrusive Gaze Tracking Using Artificial Neural Networks, Technical Report CMU-CS-94-102, Carnegie Mellon University, 1994, pp. 1-14.
S. Birchfield. An Elliptical Head Tracker, Proceedings of the 31st Asilomar Conference on Signals, Systems, and Computers, Pacific Grove, California, Nov. 1997, 5 pages.

(Continued)

*Primary Examiner*—Joseph Mancuso
*Assistant Examiner*—Alex Liew
(74) *Attorney, Agent, or Firm*—Fenwick & West LLP; Mark Duell

(57) ABSTRACT

System and methods for non-intrusive real-time eye detection and tracking are disclosed. A subject's eyes can be detected by using active illumination analysis to generate a difference image of the subject. In the difference image, the bright pupil effect intensifies the appearance of the subject's pupils. A component analysis can be used to identify a set of pupil candidates from the difference image. An appearance-based analysis can be applied to the pupil candidates to identify the subject's eyes from background noise that can occur under various lighting conditions. After the subject's eyes are detected, a multi-stage tracking process is disclosed for detecting real-time eye movements. Further features are disclosed such as an image acquisition apparatus that reduces external illumination interferences.

26 Claims, 8 Drawing Sheets

OTHER PUBLICATIONS

S. Birchfield. Elliptical Head Tracking Using Intensity Gradients and Color Histograms, Proceedings of the IEEE Conference on Computer Vision and Pattern Recognition, Santa Barbara, California, Jun. 1998, 6 pages.

G. R. Bradski. Real Time Face and Object Tracking as a Component of a Perceptual User Interface, IEEE Work on Applic. Comp. Vis., Princeton, 1998, pp. 214-219.

C. Cortes and V. Vapnik. Support-Vector Networks, Machine Learning, vol. 20, 1995, pp. 1-31.

T. Darrell et al. Active Face Tracking and Pose Estimation in an Interactive Room, IEEE Computer Society Conference on Computer Vision and Pattern Recognition, 1996, pp. 1-16.

Y. Ebisawa and S. Satoh. Effectiveness of Pupil Area Detection Technique Using Two Light Sources and Image Difference Method. Proceedings of the 15$^{th}$ Annual Int. Conf. Of the IEEE Eng. in Medicine and Biology Society, San Diego, California, 1993, pp. 1268-1269.

Y. Ebisawa. Unconstrained Pupil Detection Technique Using Two Light Sources and the Image Difference Method, Visualization and Intelligent Design in Engineering and Architecture, 1995, 11 pages.

A. W. Fitzgibbon and R.B. Fisher. A Buyer's Guide to Conic Fitting. Proceedings of the 5$^{th}$ British Machine Vision Conference, Birmingham, 1995, 10 pages.

A. Haro, et al., Detecting and Tracking Eyes By Using Their Physiological Properties, Dynamics, and Appearance. Proceedings IEEE CVPR 2000, Hilton Head Island, South Carolina, Jun. 2000, pp. 1-6.

J. D. Huang et al. Pose Discrimination and Eye Detection Using Support Vector Machines (SVM), Proceeding of NATO-ASI on Face Recognition: From Theory to Applications, 1998, pp. 1-9.

Q. Ji and X. Yang. Real Time Visual Cues Extraction for Monitoring Driver Vigilance, In Proceedings of International Workshop on Computer Vision Systems, Vancouver, Canada, Jul. 7-8, 2001, 19 pages.

C. H. Morimoto et al. Pupil Detection and Tracking Using Multiple Light Sources. Technical Report RJ-10117, IBM Almaden Research Center, 1998, pp. 331-335.

C.H. Morimoto and M. Flickner. Real-Time Multiple Face Detection Using Active Illumination, Proceedings of the 4$^{th}$ IEEE International Conference on Automatic Face and Gesture Recognition 2000, Grenoble, France, Mar. 2000, pp. 1-6.

N. Oliver et al. LAFTER: Lips and Face Time Tracker. In CVPR97, 1997, 7 pages.

P. Smith et al. Monitoring Head/Eye Motion for Driver Alertness With One Camera, Proceedings of the International Conference on Pattern Recognition (ICPR'00), Session P4.3A, 2000, 7 pages.

M. Turk and Alex Pentland. Eigenfaces for Recognition, Journal of Cognitive Neuroscience, vol. 3, No. 1, 1991, pp. 71-86.

V. N. Vapnik, The Nature of Statistical Learning Theory, Springer-Verlag New York, Inc., 1995, pp. 133-156.

V. Cherkassky et al., Learning From Data—Concepts, Theory, and Methods, John Wiley & Sons, Inc., New York, 1998, pp. 371-378.

* cited by examiner

REAL-TIME EYE DETECTION AND TRACKING UNDER VARIOUS LIGHT CONDITIONS

RELATED APPLICATION

This application is related to U.S. provisional patent application No. 60/367,878, filed on Mar. 26, 2002, entitled "Real-Time Eye Detection and Tracking Under Various Light Conditions," from which priority is claimed under 35 U.S.C. §119(e) and which application is incorporated by reference herein in its entirety.

TECHNICAL FIELD

This invention relates generally to human-machine interaction, and more particularly, to real-time eye detection and tracking.

BACKGROUND

Computer vision technology provides a powerful tool for human-machines interfaces. There are many applications that can benefit from a computer determination of human eye position and/or movements. One application, for example, is an automobile that can determine whether the driver's eyes are open and looking at the road. If the driver has fallen asleep, the automobile computer can act appropriately to restore a safe operating environment.

One conventional approach to detecting eye movements uses methods that are intrusive upon the human subject. Intrusive methods include, for example, using a chin support, a head-mounted camera, or other special devices to constrain face positioning with respect to a sensor or camera. One problem with intrusive methods is user acceptance. Users typically dislike applying an unnatural or unwelcome device in order to interface with the computer.

Other conventional approaches use non-intrusive techniques. Typical non-intrusive eye detection and tracking techniques can be classified into two mutually exclusive categories: active infrared (IR) illumination methods and appearance-based methods. An active IR technique illuminates a subject's face using an IR emitter such as a light emitting diode (LED). In certain external lighting conditions, the eye's pupil can appear brighter than the rest of the face. The active IR method uses differential IR illumination to detect the high contrast between the pupils and the rest of the face.

One problem with this technique is that its accuracy depends on the brightness and size of the pupils, which is often a function of face orientations, external illumination interferences, and the distance of the subject to the camera. Another problem with this technique is that the subject needs to be close to camera because different face orientations and distance make it more difficult to get a good differential image of the pupils. The robustness of the active IR approach, therefore, depends upon the stability of the lighting conditions and close proximity of the subject to the camera.

A typical appearance-based method detects a subject's eyes based on the intensity (or color) distribution of the eyes, which appear different from the rest of the face. Eyes can be detected and tracked based on exploiting the differences in appearance. This method usually needs to collect a large amount of training data representing the eyes of different subjects, under different face orientations, and different illumination conditions. The conventional appearance-based approach, while not requiring special illumination, can require a significant amount of training data to enumerate all possible appearances of eyes because the eye's appearance can change dramatically due to different illuminations, face orientations, or the subject's eyeglasses.

What is needed is a technique for detecting and tracking eye movements that is non-intrusive and acceptable to a user. What is further needed is a technique for detecting and tracking eye movements that is robust under various light conditions and subject positions.

SUMMARY OF THE INVENTION

One embodiment of the present invention provides real-time eye detection and tracking under variable lighting conditions. Variable lighting conditions include strong non-infrared light (e.g., conventional fluorescent room lighting). An active infrared approach is combined with an appearance-based method to achieve robust eye detection and movement tracking. A subject's eyes can be detected by using active illumination analysis to generate a difference image of the subject. In the difference image, the bright pupil effect intensifies the appearance of the subject's pupils.

In one embodiment of the present invention, images of the subject's face are acquired using an active infrared (IR) illuminator that generates a bright pupil and a dark pupil image of the subject's face. The IR illuminator advantageously incorporates a bandpass filter that improves the signal-to-noise ratio of the images. The bandpass filter can be matched to the nominal wavelength and passband of the IR illuminator.

In another embodiment of the present invention, a component analysis can be used to identify a set of pupil candidates from the difference image. The component analysis can incorporate parameters such as size, shape, or other geometry to distinguish pupil candidates from other features of the face or background noise. An appearance-based analysis can be applied to the pupil candidates to identify or to verify the location of the subject's eyes within the image. An appearance-based technique such as the pattern classification and/or recognition features of a support vector machine can be used to detect and to track the movements of the subject's pupils based on the appearance of the eye.

In a further embodiment of the present invention, a multi-stage tracking process is used to detect real-time eye movements from frame-to-frame. The first stage of the tracking process uses a conventional Kalman filtering technique to track the location of the subject's eyes from a first frame to a second frame. If the first tracking stage is unsuccessful, a second tracking stage uses a mean-shift technique on the dark pupil image to predict the subject's eye movement from the first frame to the second frame.

Further features of the invention, its nature and various advantages will be more apparent from the accompanying drawings and the following detailed description.

BRIEF DESCRIPTION OF THE DRAWINGS

The accompanying drawings illustrate several embodiments of the invention and, together with the description, serve to explain the principles of the invention.

DETAILED DESCRIPTION OF THE EMBODIMENTS

The present invention is now described more fully with reference to the accompanying figures, in which several embodiments of the invention are shown. The present invention may be embodied in many different forms and should not be construed as limited to the embodiments set forth herein. Rather these embodiments are provided so that this disclosure will be thorough and complete and will fully convey the invention to those skilled in the art.

A. System Overview

In one embodiment of the present invention, active infrared (IR) illumination and appearance-based techniques are used to perform eye detection and tracking under various light conditions, such as strong non-infrared light. Active IR illumination can be used to brighten a subject's face to produce the bright pupil effect. The bright pupil effect and appearance of eyes (e.g., a statistical distribution based on eye patterns) are used to detect and to track the subject's pupils. Pattern classification recognition (e.g., a support vector machine) and object tracking (e.g., a mean-shift process) are used for pupil detection and eye movement tracking based on the appearance of the subject's eyes.

The processes, features, or functions of the present invention can be implemented by program instructions that execute in an appropriate computing device. Example computing devices include enterprise servers, application servers, workstations, personal computers, network computers, network appliances, personal digital assistants, game consoles, televisions, set-top boxes, premises automation equipment, point-of-sale terminals, automobiles, and personal communications devices (e.g., cellular handsets).

The program instructions can be distributed on a computer readable medium or storage volume. The computer readable storage volume can be available via a public network, a private network, or the Internet. Program instructions can be in any appropriate form, such as source code, object code, or scripting code.

B. Image Acquisition

Figure 1A:
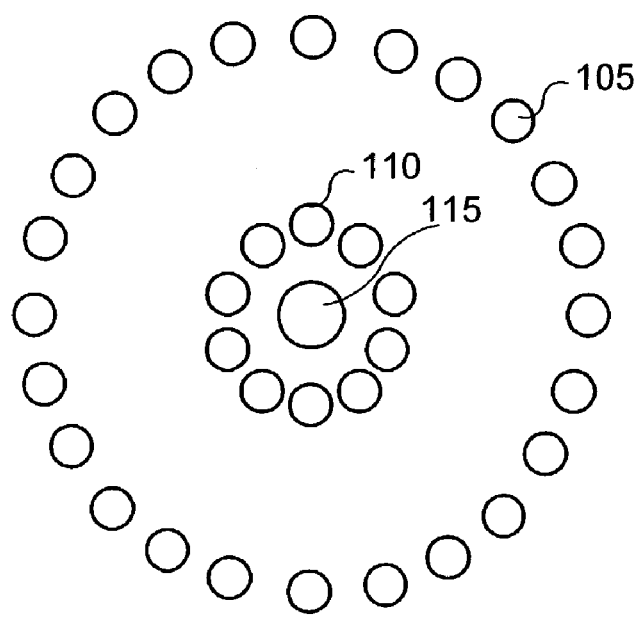
FIG. 1A is a diagram illustrating a first configuration of an infrared illuminator in accordance with the present invention.

The active illumination analysis and appearance-based analysis make use of an IR image or series of IR images of the subject's face. In general, a subject's face is illuminated with IR light and a camera captures an image of the illuminated face. FIG. 1A is a diagram illustrating a first configuration of an infrared illuminator in accordance with the present invention. The illustrated embodiment includes an outer ring 105, an inner ring 110, and a camera 115. The outer ring 105 includes a plurality of IR light emitting diodes (LEDs). The inner ring 110 also includes a plurality of IR LEDs. The outer ring 105 is positioned off the optical axis of the camera 115, while the inner ring 110 is positioned near the optical axis of the lens of the camera 115. Specifically, the inner ring 110 is positioned sufficiently close to the optical axis of the lens of the camera 115 so as to produce a bright pupil image. The outer ring 105 is positioned sufficiently far from the optical axis of the lens of the camera 115 so as to produce a dark pupil image having generally the same image characteristics (e.g., contrast and/or brightness) as the bright pupil image. The lens of the camera 115 is generally focused on the subject's face. One skilled in the art will appreciate that the mean focal distance or the distance of the subject from the camera may vary depending on the application and be adjusted accordingly. For example, in an automobile application the driver's face is likely in a range of two to six feet from a dashboard mounted illuminator. In one embodiment of the present invention, the camera 115 can be equipped with objective lenses to size or resize the subject's image.

As described in further detail below, the outer ring 105 is placed off the optical axis of the camera 115 to produce a dark pupil image of the subject. The inner ring 110 is placed on or near the optical axis of the camera 115 to produce a bright pupil image. Embodiments of the present invention use the dark pupil and the bright pupil images to detect and to track the subject's eyes.

In one embodiment of the present invention, the IR LEDs of the outer ring 105 and the inner ring 110 operate at a power of 32 mW in a wavelength band 40 nm wide at a nominal wavelength of 880 nm. The camera 115 has a maximum spectral response of approximately 880 nm, which is selected to match the nominal wavelength of the IR LEDs. The camera 115 includes an optical bandpass filter which has a wavelength pass band approximately 10 nm wide. In this embodiment of the present invention, the optical bandpass filter can increase the signal-to-noise ratio by a factor of 20 when compared to not using the filter. One benefit of the IR illuminator of the first configuration is improved image quality. The image quality can contribute to the accuracy or robustness of the subsequent image processing techniques.

Figure 1B:
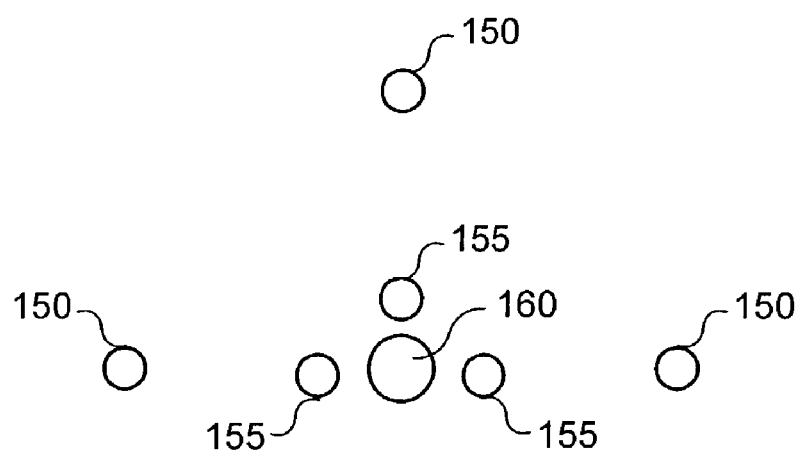
FIG. 1B is a diagram illustrating a second configuration of an infrared illuminator in accordance with the present invention.

FIG. 1B is a diagram illustrating a second configuration of an infrared illuminator in accordance with the present invention. The illustrated embodiment includes outer LEDs 150, inner LEDs 155, and a camera 160. The outer LEDs 150 and the inner LEDs 155 are disposed in a triangular configuration with respect to the camera 160. Similar to the embodiment illustrated in FIG. 1A, the outer LEDs 150 are not aligned with the optical axis of the camera 160 to produce a dark pupil image. The inner LEDs 155 are aligned with the optical axis of the camera 160 to produce a bright pupil image. Specifically, the inner LEDs 155 are positioned sufficiently close to the optical axis of the lens of the camera 160 so as to produce a bright pupil image. The outer LEDs 150 are positioned sufficiently far from the optical axis of the lens of the camera 160 so as to produce a dark pupil image having generally the same image characteristics (e.g., contrast and/or brightness) as the bright pupil image.

Although the illustration includes three LEDs for each of the outer LEDs 150 and the inner LEDs 155, one skilled in the art will appreciate that additional or fewer LEDs can be used. One example of using additional LEDs is illustrated in FIG. 1A. In the example configuration of FIG. 1B, the outer LEDs 150 and the inner LEDs 155 are positioned symmetrically about the camera 160 to produce a uniform illumination of the subject while using fewer LEDs than the example configuration shown in FIG. 1A. The benefits of using fewer LEDs include lower cost and a smaller overall footprint for the illuminator.

One skilled in the art will recognize that conventional IR illuminators such as those commercially available from SensoMotoric Instruments GmbH of Teltow, Germany can be used in an embodiment of the present invention. Although the processes, features, or functions described herein may benefit from IR illuminators such as those described above and with reference to FIGS. 1A and 1B, the embodiments of the present invention do not necessarily depend on particular IR illuminator or imaging hardware.

C. Eye Detection and Tracking

Figure 2:
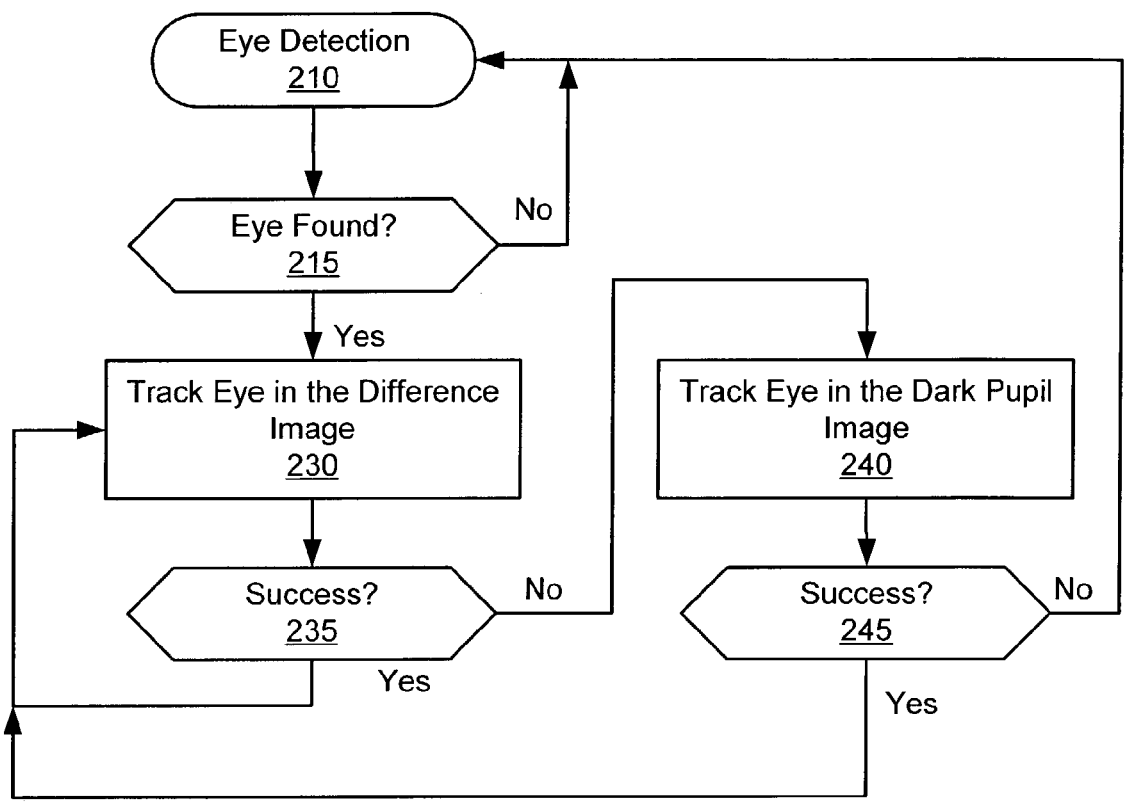
FIG. 2 is a flowchart illustrating an eye detection and tracking process according to one embodiment of the present invention.

FIG. 2 is a flowchart illustrating an eye detection and tracking process according to one embodiment of the present invention. The process illustrated in FIG. 2 represents an overall functional flowchart. Further details of the steps illustrated in FIG. 2 are described below. Generally, the illustrated process includes two stages: an eye detection stage and an eye tracking stage. In one embodiment of the present invention, the eye detection stage includes a combined active illumination and appearance-based process. The eye tracking stage includes two levels of tracking. The first level of tracking uses the difference image to track eye movements. If the first level of tracking fails to find the eyes, a second level of tracking is invoked. In the second level of tracking, the dark pupil image is analyzed to track the eye movements. If the second level of tracking fails, then the process restarts with the eye detection stage.

More specifically, the illustrated process begins with performing eye detection 210. If the subject's eyes are not found 215, eye detection 210 is repeated. One skilled in the art will recognize that parameters, such as camera focus, can be adjusted if the subject's eyes are not found 215. If the subject's eyes are found 215, the process continues to track the eyes in the difference image 230. If the difference image tracking 230 is successful 235, then the process returns to tracking the eyes in the difference image 230.

If the difference image tracking 230 is unsuccessful 235, then the process continues to track the eyes in the dark pupil image 240. If the dark pupil image tracking 240 is successful 245, then the process returns to tracking the eyes in the difference image 230. If the dark pupil image tracking 240 is unsuccessful 245, then the process restarts with eye detection 210.

In one embodiment of the present invention, the successfulness steps 235, 245 use a support vector machine accuracy calculation to determine whether the eyes are being successfully tracked from the previous image or frame. If the accuracy does not meet a predetermined threshold (e.g., 95% accurate) then the tracking result is deemed unsuccessful. A two stage tracking process is advantageous because it can achieve accurate results while balancing the use of system resources (e.g., processor time or memory) needed to perform eye detection 210 for each of a plurality of consecutive images.

Figure 3:
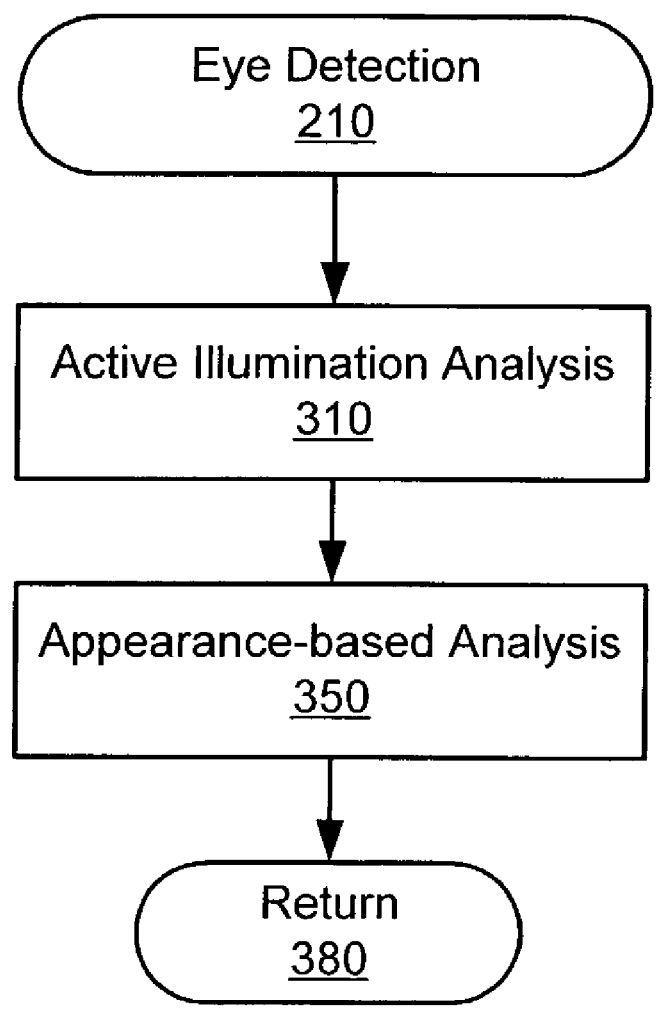
FIG. 3 is a flowchart illustrating further details of eye detection according to one embodiment of the present invention.

FIG. 3 is a flowchart illustrating further details of eye detection according to one embodiment of the present invention. The process of eye detection 210 includes active illumination analysis 310 and appearance-based analysis 350. In the embodiment of the present invention illustrated in FIG. 3, the active illumination analysis 310 is performed before the appearance-based analysis 350. In another embodiment of the present invention, the appearance-based analysis 350 can be performed before or concurrently with the active illumination analysis 310. One advantage of the illustrated configuration is that the output of the active illumination analysis 310 can be used to focus the scope of the appearance-based analysis 350, which is generally a slower or more processor intensive task. After the appearance-based analysis 350 completes, the process of eye detection 210 returns 380 to the calling process.

1. Pupil Detection

Figure 4:
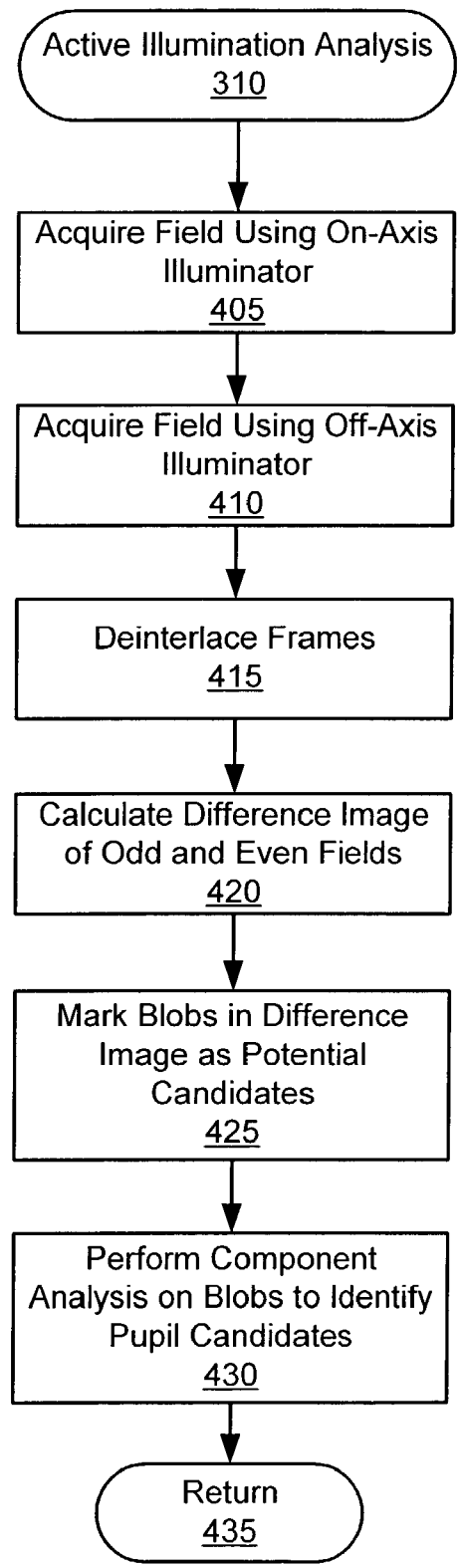
FIG. 4 is a flowchart illustrating active illumination analysis according to one embodiment of the present invention.

FIG. 4 is a flowchart illustrating active illumination analysis according to one embodiment of the present invention. In one embodiment of the present invention, the camera 115/160 captures an interlaced frame. An interlaced frame includes an odd field and an even field. In an image sequence with a frame rate of 30 frames per second, there are 60 even fields per second and 60 odd fields per second that are interlaced to produce an overall 30 frames per second. In one embodiment of the present invention, the active illuminators of FIGS. 1A and 1B can be synchronized with the even and odd fields of the camera 115/160. For example, when the camera 115 is scanning an even field, the inner ring 110 is turned on and the outer ring 105 is turned off. When the odd field is being scanned the outer ring 105 is turned on and the inner ring 110 is turned off.

The active illumination analysis 310 process begins with acquiring 405 an even field using an on-axis illuminator and acquiring 410 an odd field using an off-axis illuminator. The camera 115/160 outputs an interlaced composite signal. The composite signal is then deinterlaced 415. The deinterlacing 415 separates the frames into even fields and odd fields. Because the even field images use on-axis illumination, the subject's pupils appear significantly brighter than in the odd field images.

Figure 8:
FIG. 8 illustrates a difference image according to one embodiment of the present invention.

To eliminate the background and reduce external light illumination, a difference image is calculated 420. For each image frame, the difference image comprises the odd field subtracted from the even field. The difference image can be thresholded to further reduce the amount of background noise. The thresholding can also reduce the gray scale image to a black and white image. A conventional thresholding process includes removing pixels having an intensity lower than a predetermined threshold. One skilled in the art will appreciate that the predetermined threshold can be adjusted depending on, for example, the mean intensity of the pupil in the difference image. One example of a difference image is shown in FIG. 8.

The difference image includes pupil blobs and/or noise blobs. A blob is a grouping of adjacent pixels (or image components) that share similar characteristics (e.g., color and/or intensity). One skilled in the art will note that a blob can have an amorphous shape and that the adjacent pixels need not be contiguous. One objective of the active illumination analysis 310 is to identify pupil candidates from the blobs. The pupil candidates can be validated by subsequent appearance-based analysis 350.

Figure 9:
FIG. 9 illustrates blobs identified in the difference image of FIG. 8 according to one embodiment of the present invention.

Initially, each of the blobs is marked 425 in the difference image as a potential pupil candidate. FIG. 9 illustrates one example of blobs identified in the difference image of FIG. 8. In FIG. 9, the square or rectangular boxes illustrate the marked blobs that represent potential pupil candidates.

A connected component analysis is then performed 430 on each of the marked blobs to identify pupil candidates. One type of connected component analysis identifies the subject's pupils based on the size and/or shape of the blob. The pupil usually appears as an ellipse-like blob and conventional ellipse fitting methods can be used to extract the shape of each blob and use the shape and size to remove some blobs from further consideration. One conventional ellipse fitting technique is described in Andrew W. Fitzgibbon, et al., "A Buyers Guide to Conic Fitting," Proceedings of the 5th British Machine Vision Conference, Birmingham, England, pp. 513–522, 1995, which is incorporated by reference herein in its entirety.

One skilled in the art will recognize that other techniques can be used to identity pupil candidates or to reduce the noise blobs in the difference image. For example, a blob with a large size or a large major-to-minor axis ratio is likely not a pupil and can be removed from further consideration. In addition, the size and/or shape of a subject's pupils can be a function of the subject's distance from the camera 115/160. By determining this distance, blobs that are too small or too large to be the subject's pupils can be removed from further consideration.

Figure 10:
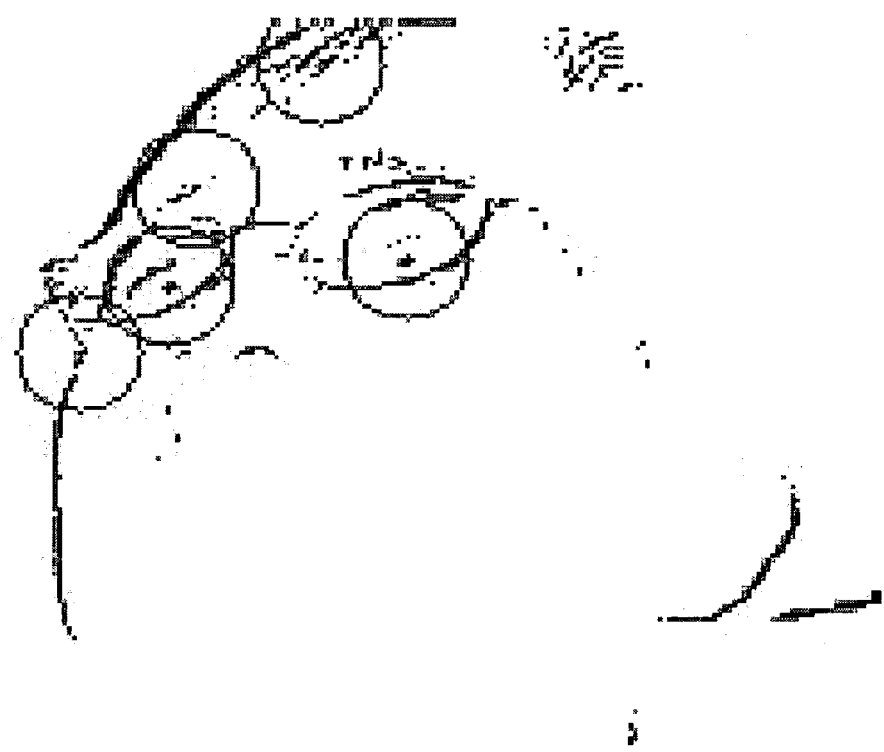
FIG. 10 illustrates pupil candidates in the difference image of FIG. 8 according to one embodiment of the present invention.

FIG. 10 illustrates one example of the results of the component analysis 430. In FIG. 10, the blobs identified for further consideration are marked with circles. After the active illumination analysis 310 identifies a set of pupil candidates, control returns 435 to the calling process. In one embodiment of the present invention, the active illumination analysis 310 can be used to focus the scope of a subsequent appearance-based analysis 350.

2. Pupil Verification

Figure 5:
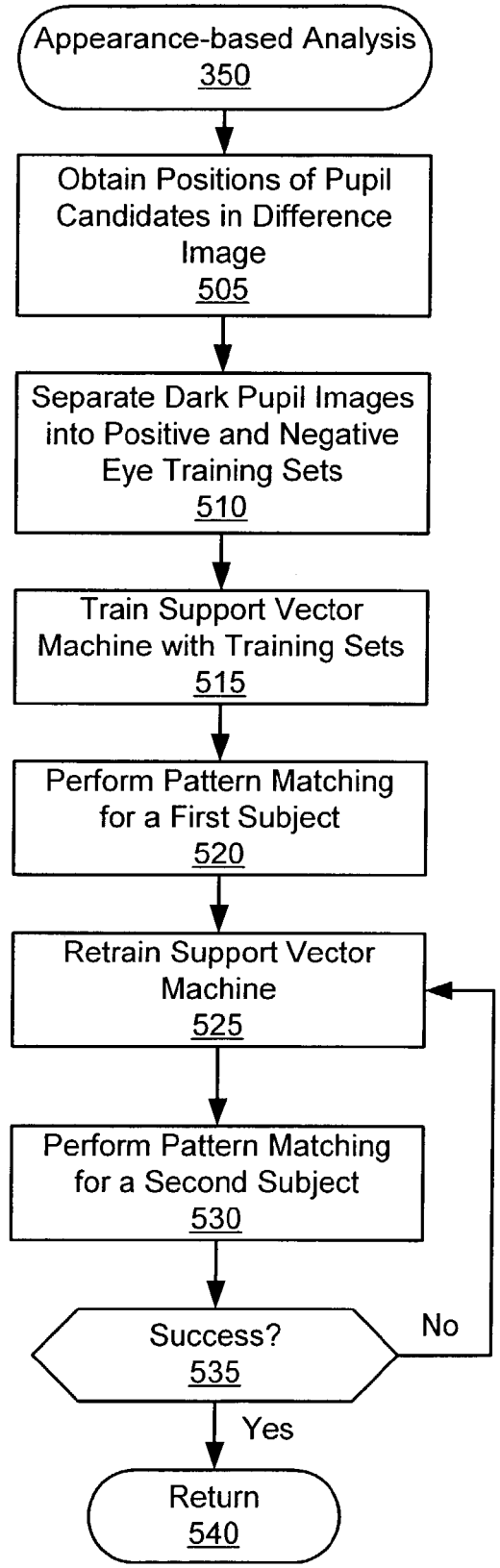
FIG. 5 is a flowchart illustrating appearance-based analysis according to one embodiment of the present invention.

FIG. 5 is a flowchart illustrating appearance-based analysis according to one embodiment of the present invention. One embodiment of the present invention uses a support vector machine (SVM) to perform the appearance-based analysis 350 that verifies the pupil candidates obtained from the active illumination analysis 310. One skilled in the art will appreciate that other pattern matching techniques can be used including, for example, neural network-based approaches.

The theoretical framework of the SVM is described briefly below so that one skilled in the art can appreciate the application of the SVM to the pattern matching techniques of the present invention. Further details of the SVM can be found in C. Cortes et al., "Support-vector networks," Machine Learning, vol. 20, pp. 273–297, 1995, which is incorporated by reference herein in its entirety.

For a case of two-class pattern recognition, the task of predictive learning from examples can be formulated as shown below in Expressions 1 and 2. Given a set of functions $f_\alpha$:

$$\{f_\alpha : \alpha \in \Lambda\}, f_\alpha : R^N \to \{-1,+1\}, \quad (1)$$

$\Lambda$ is an index set and a set of l examples $$(x_1, y_1), \ldots (x_i, y_i), \ldots, (x_l, y_l), x_i \in R^N, y_i \in \{-1,+1\} \quad (2)$$

where $x_i$ is a feature vector of N dimensions and, $y_i$ represents the class, which has only two values −1 and +1, each one generated from an unknown probability distribution $P(x,y)$, we want to find a particular function $f^*_\alpha$ which provides the smallest possible value for the risk, as defined in Expression 3. One skilled in the art will appreciate that Expression 3 can define error (or accuracy) mathematically. Table 1, which is described below, is one example of experimental results including values for accuracy.

$$R(\alpha) = \int |f_\alpha(x) - y| dP(x,y) \quad (3)$$

The SVM approach seeks separating hyper-planes $D(X)=(w \cdot X + w_0)$ by mapping the input data X into a higher dimensional space Z using a nonlinear function g. The data points at the maximum margin are called the support vectors because they define the optimal hyperplane. In one implementation, the SVM approach requires training data to obtain the optimal hyperplane. The use of training sets for pupil recognition and/or verification is described below in further detail.

Figure 11:
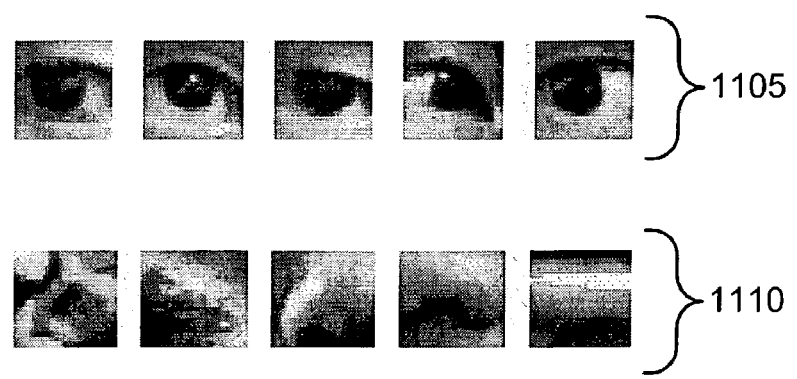
FIG. 11 illustrates example images in positive and negative training sets according to one embodiment of the present invention.

The appearance-based analysis process illustrated in FIG. 5 begins with obtaining 505 the positions of the pupil candidates identified in the difference image. In one embodiment of the present invention, active illumination analysis 310 generates a coordinate list including the positions of the pupil candidates within the difference image. These positions are applied to the dark pupil image, and positive and negative training sets are separated 510 from the dark pupil image. In one embodiment of the present invention, a 20×20 pixel image is cropped from the dark pupil image at each of the coordinate positions. The cropped images can be preprocessed using conventional histogram equalization and normalization to a [0,1] range before training. FIG. 11 illustrates one example of cropped images in the positive training set 1105 and the negative training set 1110. The positive training set 1105 includes eye images of different gazes, different degrees of opening, different subject, and with/without eyeglasses. The negative training set 1110 includes the non-eye images (i.e., portions of the nose, cheek, etc.).

The SVM is then trained 515 with the positive 1105 and the negative 1110 training sets and pattern matching is performed 520 for a first subject. One skilled in the art will appreciate that learning machines that rely only on limited labeled training sets (such as positive 1105 and negative 1110 training sets) may not achieve high learning accuracy. In order to achieve higher accuracy, the SVM is retrained 525 by labeling the data that the SVM mislabeled from the first subject. That is, if the SVM mistakenly identifies an image containing a portion of a nose as a subject's eye, the mislabeled image can be placed in the correct training group (in this example, the negative set).

Next, pattern matching is performed 530 for a second subject. If the SVM is unsuccessful 535 in identifying the eyes of the second subject, then retraining 525 is repeated using data from additional subjects. In one experiment, eye data set from six subjects were used to obtain successful results. A successful result is one that achieves a predetermined SVM accuracy (e.g., 95%). If the process is successful 535, then control returns 540 to the calling process.

One experiment generated a training set including 558 positive images and 560 negative images. One skilled in the art will appreciate that SVM parameters (e.g., the learning kernel) can be changed to maximize the accuracy. Table 1 shows experimental results for three SVM kernels with various parameters settings using 1757 candidate images. In this case, the best accuracy was 95.5037% which was achieved with the Gaussian SVM kernel whose sigma term is 3.

TABLE 1

| Kernel Type | Degree | Sigma | # Support Vectors | Accuracy |
| --- | --- | --- | --- | --- |
| Linear | | | 376 | 0.914058 |
| Polynomial | 2 | | 334 | 0.912351 |
| Polynomial | 3 | | 358 | 0.936255 |
| Polynomial | 4 | | 336 | 0.895845 |
| Gaussian | | 1 | 1087 | 0.500285 |
| Gaussian | | 2 | 712 | 0.936255 |
| Gaussian | | 3 | 511 | 0.955037 |
| Gaussian | | 4 | 432 | 0.946500 |
| Gaussian | | 5 | 403 | 0.941377 |

3. Eye Tracking

Figure 6:
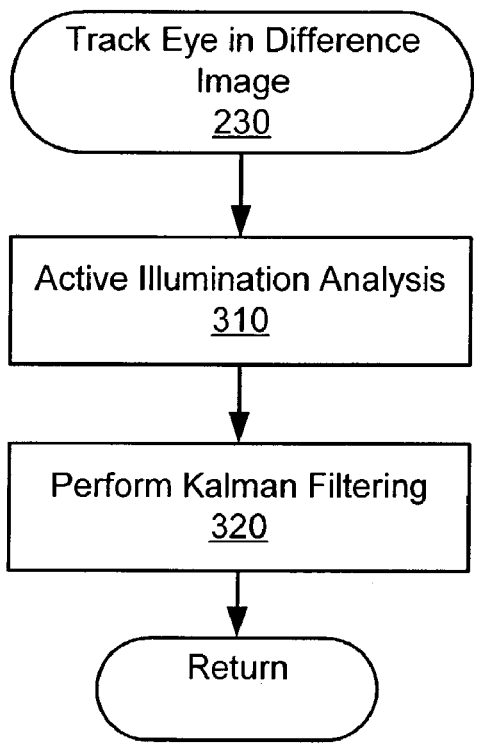
FIG. 6 is a flowchart illustrating further details of tracking an eye in a difference image according to one embodiment of the present invention.

After the eye is detected 210 from the initial frames or images from the camera 115/160, the pupils can be tracked in real-time from frame-to-frame. FIG. 6 is a flowchart illustrating further details of tracking an eye in a difference image according to one embodiment of the present invention. As described above, the tracking process includes two levels of tracking. The process illustrated in FIG. 6 describes the first level. Tracking the eye in the difference image 230 includes repeating the active illumination analysis 310 for a second image of the subject. The second image can represent another frame of a captured image sequence or a real-time frame capture. A conventional Kalman filtering analysis is then performed 320 to track the location of the eye in a localized region of where the eye was in the previous image. The Kalman filter estimates the position and uncertainty of a moving feature point in the next frame, that is, where to look for the feature and how large a region should be searched in the next frame to be sure to find the feature within a certain confidence. One conventional Kalman filtering technique is described in Q. Ji, et al., "Real time visual cues extraction for monitoring driver vigilance," Proceedings of International Workshop on Computer Vision Systems, July 2001, which is incorporated by reference herein in its entirety.

If the Kalman filtering process fails to track 230 the eye movements in the difference image, the second level of tracking is invoked. The process illustrated in FIG. 7 describes one embodiment of this second level approach. Generally, after locating the eyes in the previous frame, a target eye model is constructed based on the detected eyes in the previous frame. The location of eyes in current frame is then estimated using mean shift iterations, with the eye locations in the previous frame as the initial position, to find the location in the current image that best matches with the target model in terms of intensity distribution.

Figure 7:
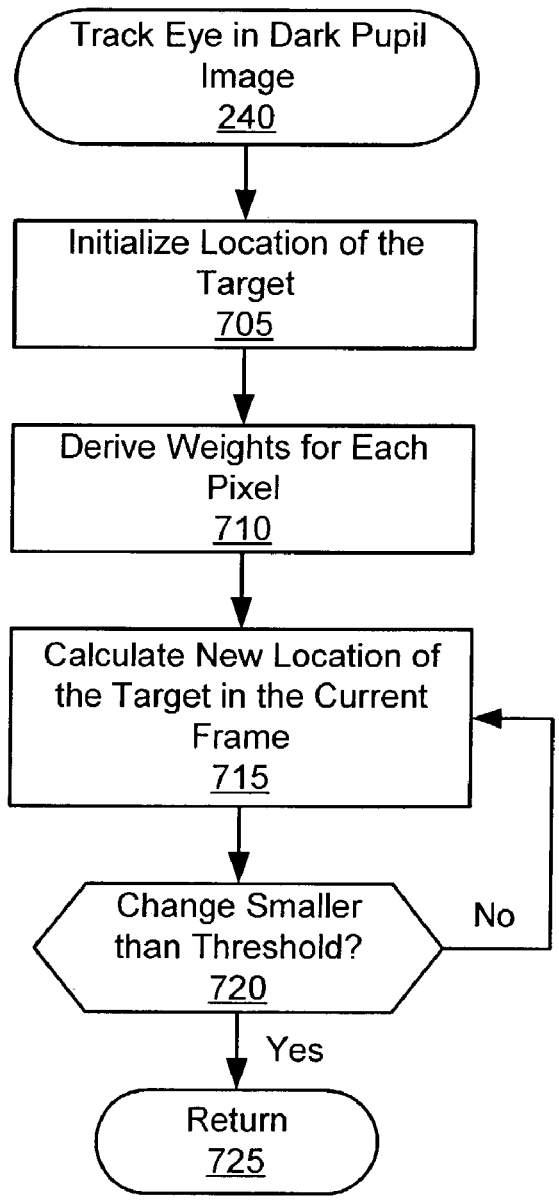
FIG. 7 is a flowchart illustrating further details of tracking an eye in a dark pupil image according to one embodiment of the present invention.

More specifically, FIG. 7 is a flowchart illustrating further details of tracking an eye in a dark pupil image using a mean shift tracking approach. The process begins with initializing 705 the location of the target to $\hat{y}_0$ in the current frame. The initial location of the target $\hat{y}_0$ is the predicted pupil position from the Kalman filter tracking process 230. Next, weights $\{w_i\}_{i=1...n}$ are derived 710 for each pixel according to Expression 4, where g is a weight function that assigns a larger value to pixel locations that are of significance and $u_i$ is the intensity of the i-th pixel. One conventional mean shift technique is described in D. Comaniciu, et al., "Real-time tracking of non-rigid objects using mean-shift," Proceedings of IEEE Conference on Computer Vision and Pattern Recognition, Hilton Head Island, S.C., 2000, which is incorporated by reference herein in its entirety.

$$w_i = g(u_i) \quad (4)$$

The new location of the target in the current frame is calculated 715 based on the mean shift vector of Expression 5, in which $X_i$ is the coordinates of i-th pixel location.

$$\hat{y}_1 = \frac{\sum_{i=1}^{n} X_i w_i}{\sum_{i=1}^{n} w_i} \quad (5)$$

If the change between the previous estimated target location and the current target location is larger than a predetermined threshold value, then the process iteratively repeats the step of calculating 715 the new location of the target in the current frame. If the change is smaller than the predetermined threshold, then the method returns 725 to the calling process. In another embodiment of the present invention, a conventional cross-correlation can be computed between the current eye images and the target eye images until the correlation coefficient meets or exceeds certain value.

Having described embodiments of real-time eye detection and tracking under various light conditions (which are intended to be illustrative and not limiting), it is noted that modifications and variations can be made by persons skilled in the art in light of the above teachings. It is therefore to be understood that changes may be made in the particular embodiments of the invention disclosed that are within the scope and spirit of the invention as defined by the appended claims and equivalents.

What is claimed is:

1. A method for identifying eyes of a subject, the method comprising the steps of:
    generating a difference image of the subject using active illumination analysis;
    identifying a set of pupil candidates from the difference image; and
    performing an appearance-based analysis with the set of pupil candidates to identify the eyes of the subject from among the pupil candidates comprising the steps of training a support vector machine with training sets having positive and negative images, and performing pattern matching for a first subject;
    retraining the support vector machine responsive to the pattern matching performed on the first subject; and
    performing pattern matching for a second subject.

2. The method of claim 1 wherein the generating step further comprises steps of:
    acquiring a first image using an on-axis illuminator; and
    acquiring a second image using an off-axis illuminator.

3. The method of claim 1 wherein the first image comprises one of an even and an odd field of a video signal.

4. The method of claim 1 wherein the second image comprises one of an even and an odd field of a video signal.

5. The method of claim 1 wherein at least one of the on-axis illuminator and the off-axis illuminator comprises an infrared emitter having a wavelength band about 40 nm wide.

6. The method of claim 1 wherein the identifying step further comprises the steps of:
    removing pixels having an intensity lower than a predetermined threshold from the difference image to identify at least one blob that represents a potential pupil candidate; and
    performing a component analysis on the at least one blob to produce the set of pupil candidates.

7. The method of claim 6 wherein the component analysis distinguishes a non-pupil blob from a pupil blob by at least one of size and shape of the at least one blob.

8. The method of claim 1 further comprising:
repeating the retraining step and the performing pattern matching for the second subject step until a determined eye identification accuracy is obtained.

9. The method of claim 1 further comprising the steps of:
generating a second difference image of the subject using active illumination; and
performing Kalman filtering on the second difference image to identify eye movement.

10. The method of claim 9 further comprising the steps of:
determining success of the eye movement identification; and
invoking dark pupil image tracking when the eye movement identification is unsuccessful.

11. The method of claim 10 wherein the step of invoking dark pupil image tracking further comprises the steps of:
initializing a target location of the eye movement in a first frame;
deriving weights for each pixel in the target location; and
calculating a predicted location of the eye movement in a second frame.

12. The method of claim 11 further comprising the steps of:
determining whether change between the target location in the first frame and the predicted location in the second frame is smaller than a predetermined threshold.

13. The method of claim 12 further comprising:
repeating the calculating of the predicted location in the second frame when the change exceeds the predetermined threshold.

14. A system for identifying eyes of a subject, the system comprising:
means for generating a difference image of the subject using active illumination analysis;
means for identifying a set of pupil candidates from the difference image; and
means for performing an appearance-based analysis with the set of pupil candidates to identify the eyes of the subject from among the pupil candidates comprising means for training a support vector machine with training sets having positive and negative images,; and
means for performing pattern matching for a first subject;
means for retraining the support vector machine responsive to the pattern matching performed on the first subject; and
means for performing pattern matching for a second subject.

15. The system of claim 14 wherein the means for generating further comprises:
means for acquiring a first image using an on-axis illuminator; and
means for acquiring a second image using an off-axis illuminator.

16. The system of claim 14 wherein the first image comprises one of an even and an odd field of a video signal.

17. The system of claim 14 wherein the second image comprises one of an even and an odd field of a video signal.

18. The system of claim 14 wherein at least one of the on-axis illuminator and the off-axis illuminator comprises an infrared emitter having a wavelength band about 40 nm wide.

19. The system of claim 14 wherein the means for identifying further comprises:
means for removing pixels having an intensity lower than a predetermined threshold from the difference image to identify at least one blob that represents a potential pupil candidate; and
means for performing a component analysis on the at least one blob to produce the set of pupil candidates.

20. The system of claim 19 wherein the component analysis distinguishes a non-pupil blob from a pupil blob by at least one of size and shape of the at least one blob.

21. The system of claim 14 further comprising:
means for repeating the retraining step and the performing pattern matching for the second subject step until a determined eye identification accuracy is obtained.

22. The system of claim 14 further comprising:
means for generating a second difference image of the subject using active illumination; and
means for performing Kalman filtering on the second difference image to identify eye movement.

23. The system of claim 22 further comprising:
means for determining success of the eye movement identification; and
means for invoking dark pupil image tracking when the eye movement identification is unsuccessful.

24. The system of claim 23 wherein the means for invoking dark pupil image tracking further comprises:
means for initializing a target location of the eye movement in a first frame;
means for deriving weights for each pixel in the target location; and
means for calculating a predicted location of the eye movement in a second frame.

25. The system of claim 24 further comprising:
means for determining whether change between the target location in the first frame and the predicted location in the second frame is smaller than a predetermined threshold.

26. The system of claim 25 further comprising:
means for repeating the calculating of the predicted location in the second frame when the change exceeds the predetermined threshold.

* * * * *